United States Patent
Ingham

(10) Patent No.: US 10,107,551 B2
(45) Date of Patent: Oct. 23, 2018

(54) PREPARATION OF SAMPLES FOR XRF USING FLUX AND PLATINUM CRUCIBLE

(71) Applicant: MALVERN PANALYTICAL B.V., Almelo (NL)

(72) Inventor: Mark Ingham, Nottingham (NL)

(73) Assignee: MALVERN PANALYTICAL B.V., Almelo (NL)

( * ) Notice: Subject to any disclaimer, the term of this patent is extended or adjusted under 35 U.S.C. 154(b) by 448 days.

(21) Appl. No.: 14/792,905

(22) Filed: Jul. 7, 2015

(65) Prior Publication Data

US 2016/0010920 A1 Jan. 14, 2016

(30) Foreign Application Priority Data

Jul. 8, 2014 (EP) ..................................... 14176193

(51) Int. Cl.
*G01N 23/223* (2006.01)
*F27D 1/00* (2006.01)
(Continued)

(52) U.S. Cl.
CPC ............ *F27D 1/0003* (2013.01); *C04B 35/01* (2013.01); *G01N 1/28* (2013.01); *G01N 23/223* (2013.01);
(Continued)

(58) Field of Classification Search
CPC ............ C04B 2235/3409; C04B 35/01; C04B 2235/3203; C04B 2235/5436;
(Continued)

(56) References Cited

U.S. PATENT DOCUMENTS 4,290,909 A * 9/1981 Takenaga ............... C09K 11/63
250/337
4,329,136 A * 5/1982 Willay ............... G01N 23/2202
425/174.8 R
(Continued)

FOREIGN PATENT DOCUMENTS

AU 2010 249 195 6/2011
CN 102 331 364 1/2012
(Continued)

OTHER PUBLICATIONS

Kenichi Nakayama and Toshihiro Nakamura: "X-ray Fluorescence Analysis of Rare Earth Elements in Rocks Using Low Dilution Glass Beads.", Analytical Sciences, vol. 21, Jul. 1, 2005 (Jul. 1, 2005), pp. 815-822, XP002731477, * the whole document *.

*Primary Examiner* — Irakli Kiknadze
(74) *Attorney, Agent, or Firm* — Leason Ellis LLP

(57) ABSTRACT

A method of of preparing samples for XRF using a flux and a platinum crucible includes forming the flux into a free-standing crucible liner. This may be achieved by mixing lithium borate particles with a liquid to form a paste; placing the lithium borate paste onto the inner surface of a mould; and after drying removing from the mould and firing the lithium borate paste to dry the lithium borate to form a free-standing crucible liner. The liner may be placed within a platinum crucible and then a sample placed in the liner. The temperature of the crucible is raised to a sufficient temperature that any oxidation reaction takes place before taking the temperature above the melting temperature of the flux to melt the crucible liner and dissolve the sample into the flux. The crucible can then be cooled and XRF measurements made on the sample.

12 Claims, 1 Drawing Sheet

(51) Int. Cl.
*C04B 35/01* (2006.01)
*G01N 1/28* (2006.01)
*F27B 14/08* (2006.01)
*F27B 14/10* (2006.01)
*C01B 35/12* (2006.01)

(52) U.S. Cl.
CPC ..... *C01B 35/121* (2013.01); *C04B 2235/3203* (2013.01); *C04B 2235/3409* (2013.01); *C04B 2235/5436* (2013.01); *C04B 2235/606* (2013.01); *C04B 2235/656* (2013.01); *F27B 2014/0843* (2013.01); *F27B 2014/104* (2013.01); *G01N 2223/307* (2013.01)

(58) Field of Classification Search
CPC ......... C04B 2235/606; C04B 2235/656; F27B 2014/0843; F27B 2014/104; F27D 1/0003; G01N 1/28; G01N 2223/307; G01N 23/223; C01B 35/121; C01B 35/12; H01L 2924/00; H01L 2924/00014; H01L 2224/48091; H01L 2924/181; H01L 2224/45144; H01L 2224/45015; H01L 2924/00012; H01L 2924/12041; H01L 2924/12042; H01L 2224/45124; H01L 2924/12044; H01L 33/502; H01L 2224/48247; A61K 31/5377; A61K 31/404; A61K 31/423; A61K 45/06; A61K 31/437; A61K 31/4439; A61K 31/4025; A61K 31/4178; A61K 31/4184; A61K 31/4525; A61K 31/454; C30B 29/22; C30B 7/10; C30B 7/14; G02F 1/3551; C09J 2425/005; C09J 7/401; C09J 7/403
USPC .............................................. 378/44–50, 70
See application file for complete search history.

(56) References Cited

U.S. PATENT DOCUMENTS 4,708,836 A * 11/1987 Gain ..................... G09B 23/30
264/222
4,871,309 A * 10/1989 Chapman ................. G01N 1/44
432/156
2012/0132472 A1* 5/2012 Las Navas Garcia .... B01L 3/04
177/1

FOREIGN PATENT DOCUMENTS

CN 102838125 A * 12/2012
GB 1203384 A * 8/1970 ......... G01N 23/2202

* cited by examiner

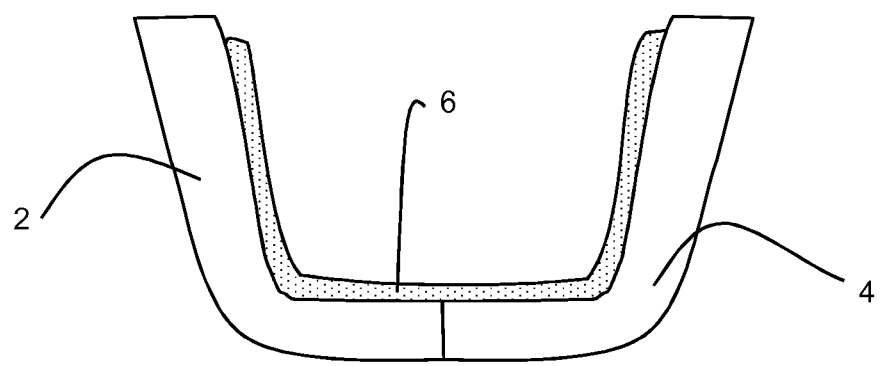

PREPARATION OF SAMPLES FOR XRF USING FLUX AND PLATINUM CRUCIBLE

FIELD OF INVENTION

The invention relates to a lithium borate crucible liner as well as to a method of making a lithium borate crucible liner and a method of use of a lithium borate crucible liner.

BACKGROUND TO THE INVENTION

In order to make X-ray fluorescence, XRF, measurements, samples need to be prepared. The sample may be powdered and placed in a platinum or gold crucible with flux. The crucible is heated to a temperature at which the flux is liquid and the sample dissolves in the flux. The melt is then cooled leaving a glassy 'bead' on the inside of the crucible or casting dish with the elements of the sample dispersed inside the deposit as a solid solution. XRF measurements may then be made on the deposit or bead.

A problem can however occur with some materials which are highly reactive. In particular, where the sample is highly reactive the sample can undergo a highly exothermic reaction process with oxygen leading to damage to the platinum crucible.

To address this issue, a procedure was proposed by Rutherford. A flux material is placed in a platinum crucible without the sample and heated in a furnace to above the temperature at which the flux melts. The crucible is then removed from the furnace and rotated around to be cooled by ambient air for sufficient time for a glassy flux surface to form in the crucible. The sample is then added to the crucible inside the glassy flux surface and heated in the furnace.

This procedure however is both difficult and dangerous since the very hot crucible at a temperature above 1000° C. is typically rotated outside the furnace by hand. This method accordingly is rarely used except by the most experienced scientists.

There accordingly remains a need for a safer and easier way of preparing XRF samples for analysis of reactive materials.

CN102331364A teaches a melted sampling method for preparing aluminium magnesium calcium iron alloy samples. A lithium tetraborate wall of a platinum crucible is first prepared. AU 2010 249 195 teaches a composition of X-ray flux including lithium borate.

SUMMARY OF THE INVENTION

According to a first aspect of the invention there is provided a method of manufacturing a crucible liner according to claim 1.

By manufacturing a free-standing crucible liner of flux in this way an improved XRF sample preparation is possible. Normally, flux is simply placed in the platinum crucible together with the sample. The inventors have however realised that it is possible to form the flux into a protective liner which can be used to protect the platinum crucible from damage before raising the temperature to the melting temperature of the flux to allow the sample to be taken up in the flux.

In particular, the improved XRF sample preparation method may include:
placing the lithium borate liner in a platinum crucible;
placing a sample in the lithium borate liner;
raising the temperature of the sample in the crucible to a reaction temperature and oxidising the sample without substantially reacting with the lithium liner; and
raising the temperature of the sample in the crucible to a fusing temperature at which the lithium borate liner acts as a flux and dissolves the oxidised sample.

In this way, the lithium crucible liner protects the platinum crucible from any reaction taking place at the reaction temperature. After the reaction is complete, the temperature may be raised again to the fusing temperature to obtain the sample dissolved in the flux.

After preparing the sample, XRF measurements may be performed on the sample.

Although a number of different flux materials are known, experiments suggest that a particularly effective crucible liner may be made from substantially pure pre-fused lithium tetraborate ($Li_2B_4O_7$).

To allow the crucible liner to be free-standing, i.e. to maintain its shape and thickness after the firing step so it can be removed from the mould, the particle size should not be too high. Accordingly, at least 50% of the lithium borate particles have a size less than 100 µm. Preferably, at least 80% of the borate particles have a size less than 100 µm. If the lithium borate particles are too large, they may be ground to provide the correct particle size.

The mould may be a two part mould which may be separated after firing to allow the fired crucible liner to be removed. Thus, preferred embodiments use a mould with at least two parts. Alternative embodiments use injection of slurry or slip.

Any suitable material may be used for the mould, but particular embodiments use silicone.

In preferred embodiments, the method further includes a separate step of drying the lithium borate paste on the inner surface of the mould before the step of firing the lithium borate paste.

The step of drying the lithium borate is carried out at a temperature of 70° C. to 200° C. for at least 5 hours, for example up to 20 hours. This step may be carried out overnight. The flux liner may then be removed from the mould before futher treatment. The inventors have found that this initial drying step results in a flux liner having a better structure. Without wishing to be bound by theory, they believe that the presence of water in subsequent processing stages can cause problems as the water boils to form bubbles. By drying the lithium borate first, these problems can be reduced.

A two stage firing process may be used, in which the step of firing the lithium borate paste comprises:
igniting the lithium borate in a furnace at a first temperature for a first period of time; and
raising the temperature in the furnace to a second temperature for a second period of time.

In a particular method, the first temperature may be 400° C. to 600° C. and the first period of time may be from 1 to 10 minutes.

The second temperature may be 600° C. to 750° C. and the second period of time may be from 5 to 20 minutes.

In another aspect, the invention relates to a crucible liner having a cup-shaped form and being made of lithium borate.

BRIEF DESCRIPTION OF THE DRAWINGS

An example of the invention will now be described with reference to the accompanying diagrams, in which:

FIG. 1 is an illustration of a mould 2, 4, with a crucible liner 6 being formed inside.

DETAILED DESCRIPTION

A specific example of a method using the invention will now be described.

A commercial sample of prefused lithium tetraborate ($Li_2B_4O_7$) flux was obtained. This was then ground in a mill to obtain a particle size distribution with 91% of the particles below 100 μm measured using a sieve method.

A spatula scoop of polyvinyl alcohol (PVA) was mixed with 100 ml reverse osmosis (RO) water.

7 g of the ground lithium tetraborate flux was mixed in an agate pestle and mortar with 2 ml of the PVA/water mix to form a paste.

A two part mould of silicone had two mould parts 2, 4. A paste 6 was coated on the inner face of the mould, to an approximately uniform thickness. The lithium tetraborate was then dried overnight in the mould at 105° C. The flux liner was removed from the mould and was transferred to a muffle furnace for firing, by igniting at 500° C. for 5 minutes, followed by increasing the temperature to 700° C. for 10 minutes.

Note that at this stage the temperature has not reached the melting point of the flux and so the particles of the flux remain intact. However, the temperature used is sufficient to burn off any carbon present, for example from the PVA.

In the case that a mould is used that can withstand the firing temperatures used, the flux liner may be left in the mould during the first/firing step.

The flux liner was allowed to cool leaving a crucible liner 6 of lithium tetraborate flux. The liner was self supporting and free standing. As a result of the process used, the liner had a thicker base than sidewalls which results in a greater quantity of the flux being at the base of the crucible where required for the next steps.

To use the flux liner, the liner was placed inside a platinum crucible. A ground sample was placed inside the liner.

The platinum crucible and contents were then placed in a furnace and heated to a temperature high enough to cause the sample to oxidise but at which the flux liner remains solid. The sample oxidised violently. However, the platinum crucible was not damaged by the reaction since it was protected by the flux liner.

After the sample reaction had completed, the temperature was raised until slightly above the temperature at which the flux liquifies. Since the melting temperature of lithium tetraborate is 920° C. a temperature range of at least 920° C. up to about 1050° C. or at most 1100° C. is suitable. The sample dissolved into the flux. The temperature was then allowed to fall leaving a glassy residue suitable for XRF measurement.

The glassy sample was placed in an XRF apparatus and the elemental composition obtained.

The approach is suitable for a wide range of samples including geo-environmental and allied materials, ceramics, minerals, industrial minerals, ores, building materials, organic matter, sulphides, metals, ferro-alloys, carbides, nitrides and others.

It will be appreciated that the above method is purely by way of example and alternatives are known.

The specific flux used and powder grain size may be varied as required. In particular, lithium metaborate ($LiBO_2$) may also be used though experiments have found that this gives a less mechanically strong flux liner.

Mixtures may also be used—the flux used may also include additions of other flux materials, including by way of example lithium bromide. The additional materials may be added to form part of the flux liner.

Alternatively, additional flux materials may be added within the liner in the crucible together with the sample. Thus, by stocking a crucible liner of lithium tetraborate variable percentages of additional fluxes such as lithium metaborate may be provided in the crucible simply by adding the additional flux together with the sample. For example, to achieve a flux of 80% lithium tetraborate and 20% lithium metaborate, a mass of lithium metaborate of 25% of the mass of a lithium tetraborate flux liner may be placed inside the flux liner in the crucible, so that in the resulting melt 20% of the flux is lithium metaborate.

The various temperatures used in the firing step may be varied as appropriate determined by experiment.

Different mould materials may be used if required.

The crucible liner may be used for moulds of other material than platinum if these are in use for any application.

The process described above uses a two-step firing process. However, it may be possible to use only a single firing step at a single temperature, which may be in the range 450° C. to well below the melting temperature of the flux, and preferably below 750° C.

Where a mixture is used as the flux, the melting temperature of the flux may be different to that of pure lithium tetraborate and accordingly a different temperature may be used to melt the flux and dissolve the sample in the flux to obtain the glassy sample.

Although the samples made are particulary suitable for XRF, they may be used in other applications if required.

The invention claimed is:

1. A method of manufacturing a crucible liner, comprising:
    mixing lithium borate particles with a liquid to form a paste;
    placing the lithium borate paste onto the inner surface of a mould;
    drying the lithium borate paste on the inner surface of the mould;
    firing the lithium borate paste to form a free-standing crucible liner that maintains its shape and thickness, wherein either
    (i) the dried lithium borate paste is removed from the mould before the step of firing the lithium borate paste, or
    (ii) the mould is configured to withstand the firing temperature and the dried lithium borate paste is left in the mould during the firing step then the fired crucible liner is removed from the mould.

2. A method according to claim 1 wherein the lithium borate is substantially pure lithium tetraborate.

3. A method according to claim 1 wherein at least 50% of the lithium borate particles have a size less than 100 μm.

4. A method according to claim 1 wherein the mould has at least two parts.

5. A method according to claim 1 wherein the mould is of silicone.

6. A method according to claim 1 wherein the step of drying the lithium borate is carried out at a temperature of 70° C. to 200° C. for at least 5 hours.

7. A method according to claim 1, wherein the step of firing the lithium borate paste comprises:
    igniting the lithium borate in a furnace at a first temperature of 400° C. to 600° C. for a first period of time of 1 to 10 minutes; and raising the temperature in the furnace to a second temperature of 600° C. to 700° C. for a second period of time of 5 to 20 minutes.

8. A crucible liner configured to be free-standing, the crucible liner having a cup-shaped form and a thicker base than the sidewalls and being made of lithium borate.

9. A crucible liner according to claim 8 wherein the crucible liner has a granular structure of particles joined to make up the cup-shaped form and wherein at least 50% of the particles have a size of less than 100 µm.

10. A crucible liner according to claim 8 wherein the lithium borate liner is substantially pure lithium tetraborate.

11. A method of use of a free-standing crucible liner having a cup-shaped form and being made of lithium borate in an X-ray fluorescence sample preparation method, the method comprising:
- placing the lithium borate liner in a platinum crucible;
- placing a sample in the lithium borate liner;
- raising the temperature of the sample in the crucible to a reaction temperature and oxidising the sample without substantially reacting with the lithium liner; and
- raising the temperature of the sample in the crucible to a fusing temperature at which the lithium borate liner acts as a flux and dissolves the oxidised sample.

12. A method according to claim 11 further comprising carrying out X-ray fluorescence measurements on the reacted oxidised sample.

* * * * *